United States Patent [19]

Hüglin et al.

[11] Patent Number: 5,955,060

[45] Date of Patent: Sep. 21, 1999

[54] BIS(RESORCINYL)TRIAZINES USEFUL AS SUNSCREENS IN COSMETIC PREPARATIONS

[75] Inventors: Dietmar Hüglin, Freiburg, Germany; Elek Borsos, Birsfelden, Switzerland; Helmut Luther; Bernd Herzog, both of Grenzach-Wyhlen, Germany; Frank Bachmann, Freiburg, Germany

[73] Assignee: Ciba Specialty Chemicals Corporation, Tarrytown, N.Y.

[21] Appl. No.: 08/752,294

[22] Filed: Nov. 19, 1996

[30] Foreign Application Priority Data

Nov. 23, 1995 [DE] Germany ............... 195 43 730

[51] Int. Cl.⁶ .................. A61K 7/42; C07D 251/24
[52] U.S. Cl. .................. 424/59; 424/60; 544/211; 544/212; 544/216
[58] Field of Search .................. 544/211, 212, 544/216; 424/59, 60

[56] References Cited

U.S. PATENT DOCUMENTS

| | | | |
|---|---|---|---|
| 3,444,164 | 5/1969 | Luethi et al. | 260/248 |
| 3,641,213 | 2/1972 | Rodgers | 260/895 |
| 3,845,049 | 10/1974 | Piller | 260/248 |
| 3,870,519 | 3/1975 | Piller | 96/51 |
| 3,896,125 | 7/1975 | Helmo et al. | 260/249.5 |
| 4,826,978 | 5/1989 | Migdal et al. | 544/216 |
| 5,182,389 | 1/1993 | Burdeska | 544/219 |
| 5,300,414 | 4/1994 | Leppard | 430/507 |
| 5,354,794 | 10/1994 | Stevenson et al. | 524/100 |
| 5,489,503 | 2/1996 | Toan | 430/507 |

FOREIGN PATENT DOCUMENTS

| | | |
|---|---|---|
| 778788 | 2/1968 | Canada . |
| 0165608 | 12/1985 | European Pat. Off. . |
| 0497734 | 8/1992 | European Pat. Off. . |
| 0685224 | 12/1995 | European Pat. Off. . |
| 4105923 | 8/1992 | Germany . |
| 4340725 | 6/1994 | Germany . |
| 0480090 | 12/1969 | Switzerland . |
| 0484695 | 3/1970 | Switzerland . |
| 2286774 | 8/1995 | United Kingdom . |
| 94/05645 | 3/1994 | WIPO . |
| 9418278 | 8/1994 | WIPO . |

OTHER PUBLICATIONS

Helvetica Chimica Acta 55(1), 1568 In German 1972.
Elvers, B. et al : Ullman's Encylopedia of Industrial Chemistry 20, 470(1992).
Chem. Abstracts, 68, 79140f (1968).
Chem. Abstracts, 115, 1613895s (1991).
Chem. Abstracts, 68, 79141g (1968).
Leppard et al., CA 119:82785, 1992.
Duennenberger ee al., CA 72:90534, 1969.

*Primary Examiner*—Yogendra N. Gupta
*Attorney, Agent, or Firm*—Kevin T. Mansfield; Jacob M. Levine

[57] ABSTRACT

There are described bis(resorcinyl)triazines of the formula

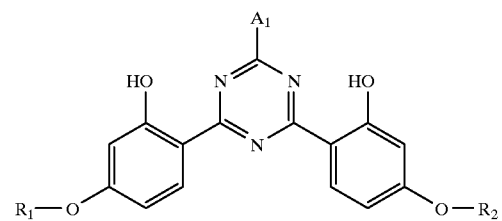

(1)

The compounds according to the invention are particularly suitable as sunscreens in cosmetic, pharmaceutical and veterinary medicinal preparations.

10 Claims, No Drawings

BIS(RESORCINYL)TRIAZINES USEFUL AS SUNSCREENS IN COSMETIC PREPARATIONS

The present invention relates to novel bis(resorcinyl) triazines, processes for the preparation of these compounds and the use of selected bis(resorcinyl)triazines for cosmetic compositions.

The novel bis(resorcinyl)triazines have the formula

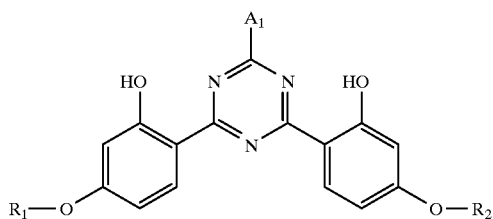
(1)

in which $R_1$ and $R_2$, independently of one another, are $C_3$–$C_{18}$alkyl; $C_2$–$C_{18}$alkenyl; a radical of the formula —$CH_2$—CH(—OH)—$CH_2$—O—$T_1$; or $R_1$ and $R_2$ are a radical of the formula

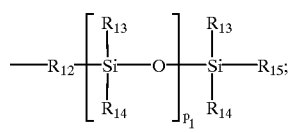
(4a)

$R_{12}$ is a direct bond; a straight-chain or branched $C_1$–$C_4$alkylene radical or a radical of the formula

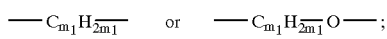

$R_{13}$, $R_{14}$ and $R_{15}$, independently of one another, are $C_1$–$C_{18}$alkyl; $C_1$–$C_{18}$alkoxy or a radical of the formula

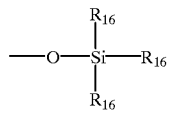

$R_{16}$ is $C_1$–$C_5$alkyl;

$m_1$ is 1 to 4;

$p_1$ is 0 or a number from 1 to 5;

$A_1$ is a radical of the formula

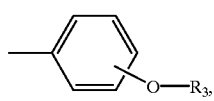
(1b)

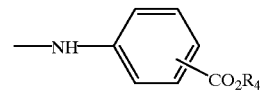
(1c)

or of the formula

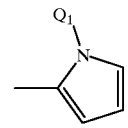
(1d)

$R_3$ is hydrogen; $C_1$–$C_{10}$alkyl, —$(CH_2CHR_5$—O$)_{n_1}$—$R_4$; or a radical of the formula —$CH_2$—CH(—OH)—$CH_2$—O—$T_1$;

$R_4$ is hydrogen; M; $C_1$–$C_5$alkyl; or a radical of the formula —$(CH_2)_{m_2}$—O—$T_1$;

$R_5$ is hydrogen; or methyl;

$T_1$ is hydrogen; or $C_1$–$C_8$alkyl;

$Q_1$ $C_1$–$C_{18}$alkyl;

M is a metal cation;

$m_2$ is 1 to 4; and $n_1$ is 1–16.

$C_1$–$C_5$alkyl, $C_1$–$C_8$alkyl, $C_1$–$C_{10}$alkyl, and $C_3$–$C_{18}$alkyl are straight-chain or branched alkyl radicals such as methyl, ethyl, n-propyl, isopropyl, n-butyl, sec-butyl, tert-butyl, amyl, isoamyl or tert-amyl, heptyl, octyl, isooctyl, nonyl, decyl, undecyl, dodecyl, tetradecyl, pentadecyl, hexadecyl, heptadecyl or octadecyl.

$C_2$–$C_{18}$alkenyl is, for example, allyl, methallyl, isopropenyl, 2-butenyl, 3-butenyl, isobutenyl, n-penta-2,4-dienyl, 3-methyl-but-2-enyl, n-oct-2-enyl, n-dodec-2-enyl, iso-dodecenyl, n-dodec-2-enyl or n-octadec-4-enyl.

Preferred bisresorcinyl compounds of the formula (1) are those in which $A_1$ is a radical of the formula

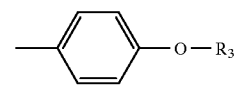
(1a₁)

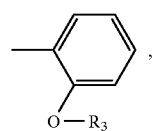
(1a₂)

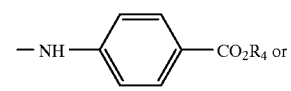
(1b₁)

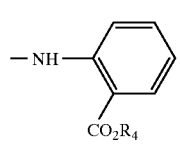
(1b₂)

$R_3$ and $R_4$ here are as defined in the formulae (1a) and (1b).

Important bisresorcinyl compounds according to the invention have the formula

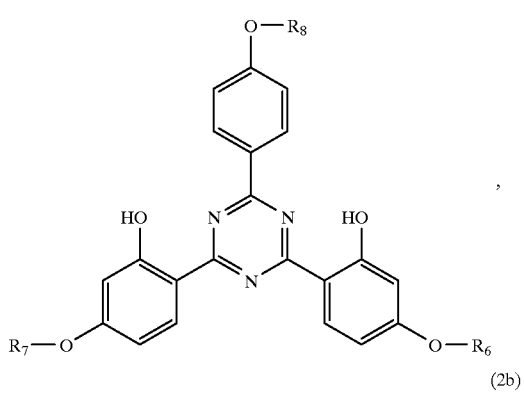

(2a)

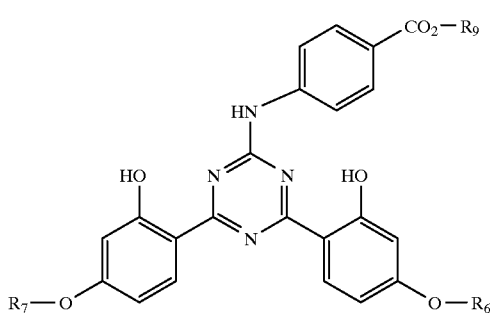

(2b)

the formula

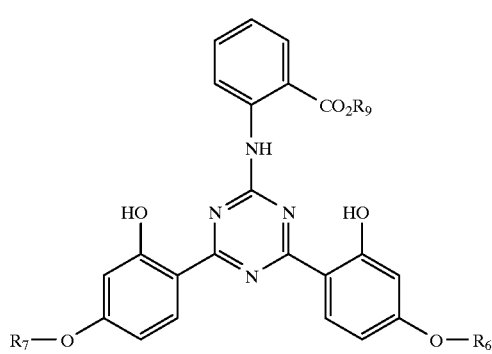

(3a)

or the formula (3b)

in which

R₆ and R₇, independently of one another, are $C_3$–$C_{18}$alkyl; or —CH₂—CH(—OH)—CH₂—O—T₁;

R₈ is $C_1$–$C_{10}$alkyl or a radical of the formula

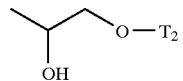

(2a₁)

, or the formula

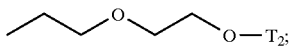

(2a₂)

R₉ is hydrogen; M; $C_1$–$C_5$alkyl; or a radical of the formula —(CH₂)$_m$—O—T₂;

T₁ and T₂, independently of one another, are hydrogen; or $C_1$–$C_5$alkyl; and m is 1 to 4.

Uppermost of interest are compounds of the formulae (2a) and (2b), in which

R₆ and R₇, independently of one another, are $C_3$–$C_{18}$alkyl; or —CH₂—CH(—OH)—CH₂—O—T₁;

R₈ is $C_1$–$C_{10}$alkyl;

and compounds of the formulae (3a) and (3b), in which

R₆ and R₇, independently of one another, are $C_3$–$C_{18}$alkyl or —CH₂—CH(—OH)—CH₂—O—T₁; and T₁ is hydrogen; or $C_1$–$C_5$alkyl.

Very particularly preferred in this case are triazine compounds of the formula (2) or (3), in which R₆ and R₇ have the same meaning.

Examples of compounds of the formula (1) which may be mentioned are:

2-(4'-methoxyphenyl)-4,6-bis(2'-hydroxy-4'-n-octyloxyphenyl)-1,3,5-triazine;

2,4-bis{[4-(3-(2-propyloxy)-2-hydroxypropyloxy)-2-hydroxy]phenyl}-6-(4-methoxyphenyl)-1,3,5-triazine;

2,4-bis{[4-(2-ethylhexyloxy)-2-hydroxy]phenyl}-6-[4-(2-methoxyethylcarboxyl)phenylamino]-1,3,5-triazine;

2,4-bis{[4-(tris(trimethylsiloxysilylpropyloxy)-2-hydroxy]phenyl}-6-(4-methoxyphenyl)-1,3,5-triazine;

2,4-bis{[4-(2"methylpropenyloxy)-2-hydroxy]phenyl}-6-(4-methoxyphenyl)-1,3,5-triazine;

2,4-bis{[4-(1',1',1',3',5',5',5'-heptamethyltrisilyl-2"-methylpropyloxy)-2-hydroxy]phenyl}-6-(4-methoxyphenyl)-1,3,5-triazine;

2,4-bis{[4-(3-(2-propyloxy)-2-hydroxypropyloxy)-2-hydroxy]phenyl}-6-[4-ethylcarboxyl)phenylamino]-1,3,5-triazine; or 2,4-bis{[4-(2-ethylhexyloxy)-2-hydroxy]phenyl}-6-(1-methylpyrrol-2-yl)-1,3,5-triazine.

The novel bis(resorcinyl)triazines can be prepared in various ways. For example, the compounds of the formula (1), if A₁ is a radical of the formula (1a) and R₁ and R₂ have the same meaning, can be prepared in a three-step reaction, starting from cyanuric chloride. In this case the appropriate phenylmagnesium bromide compound is reacted in a Grignard reaction with cyanuric chloride to give the dichlorotriazine compound of the formula

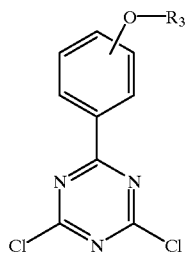
(1d)

Processes for the preparation of these intermediates are known and described, for example, in EP-A-0,577,559. The two resorcinyl groups are then introduced in a generally known manner by Friedel-Crafts acylation of resorcinol in the presence of a Lewis acid, in particular aluminium chloride. In the third step, the etherification of the free p-hydroxyl groups is carried out, depending on the meaning of the radicals $R_1$ and $R_2$, by alkylation or acid-catalysed addition of glycidyl ethers. Detailed information for this can be taken from the preparation examples.

The dichlorotriazine intermediate of the formula (1d) is also accessible by ring closure reaction without use of a Grignard reagents. To this end, the appropriately substituted benzonitrile is reacted with dicyandiamide to give the 6-aryl-1,3,5-triazine-2,4-dione, which is converted using thionyl chloride into the chloro derivative of the formula (1d). Alternatively to this, the compound of the formula (1d) is also accessible by reaction of the appropriately substituted N,N-dimethylcarboxamides with phosphorus oxychloride and N-cyanochloroformamidine. These reactions are already known and are described, for example, in Dyes and Pigments 7, 419–443 (1986).

Compounds of the formula (1), in which $A_1$ is a radical of formula (1a), can furthermore be obtained by reaction of phenyl-substituted benzoxazin-4-ones of the formula

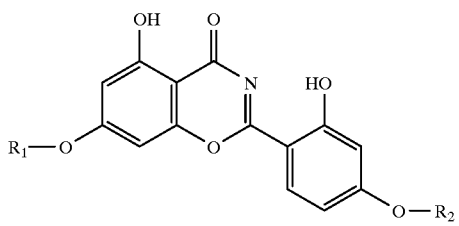
(1e)

with benzamidine compounds of the formula

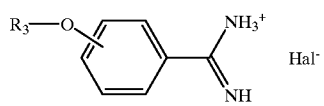
(1f)

where $R_1$, $R_2$ and $R_3$ are as defined. The preparation of such benzoxazinone intermediates and the reaction with amidines are described in Helv.Chim.Acta 55, 1566–1595 (1972).

If in formula (1) $A_1$ is a radical of the formula (1b) and $R_1$ and $R_2$ have the same meaning, the bis(resorcinyl)triazines according to the invention can be prepared, for example, in a three-step reaction, starting from cyanuric chloride. In this case the appropriate aminobenzoic acid ester is reacted with cyanuric chloride to give the dichlorotriazine compound of the formula

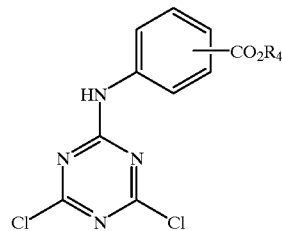
(1g)

The two resorcinol groups are then introduced in a generally known manner by Friedel-Crafts acylation of resorcinol in the presence of a Lewis acid, in particular aluminium chloride. These reactions are described, for example, in EP-A-165,608. Finally, the free p-hydroxyl groups are etherified, depending on the meaning of the radicals $R_1$ and $R_2$, by alkylation or acid-catalysed addition of glycidyl ethers. Detailed information for this can be taken from the synthesis examples.

Furthermore, the compounds of the formula (1) according to the invention can be prepared by dehydration of a dihydrotriazine compound of the formula

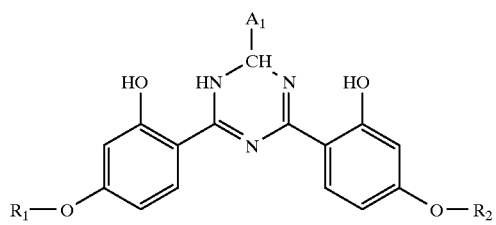
(1h)

$R_1$, $R_2$ and $A_1$ are as defined in formula (1).

The dehydrating agent generally employed is chloranil. The dehydration of dihydrotriazine compounds to give 1,3,5-triazines with the aid of chloranil is known, for example, from Khim. Geteritsikl. Soedin. (2), pp. 350–353 (1969).

Compounds of the formula (1), in which $A_1$ is a radical of the formula (1c) and $R_1$ and $R_2$ have the same meaning, can be prepared, for example, in a three-step reaction, starting from cyanuric chloride. In this case the appropriate N-alkylpyrrole is reacted selectively with cyanuric chloride in a Friedel-Crafts reaction to give the dichlorotriazine compound of the formula

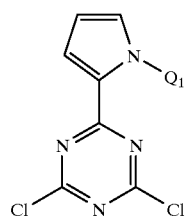
(1i)

$Q_1$ in this case is as defined in formula (1).

The two resorcinol groups are then introduced in a generally known manner by Friedel-Crafts acylation of resorcinol in the presence of a Lewis acid, in particular aluminium chloride. These reactions are described, for example, in EP-A-165,608. The free p-hydroxyl groups are etherified by alkylation or acid-catalysed addition of glycidyl ethers. Detailed information for this can be taken from the synthesis examples.

The compounds of the formula (1) according to the invention and other selected bis(resorcinyl)triazine compounds known from the prior art are particularly suitable as UV filters, i.e. for protecting ultraviolet-sensitive organic materials, in particular the skin and hair of humans and animals, from the harmful effects of UV radiation. These compounds are therefore suitable as sunscreens in cosmetic, pharmaceutical and veterinary medical preparations. These compounds can be used both in dissolved form and in the micronized state.

A further subject of the invention is therefore a cosmetic preparation, comprising at least one compound of the formula

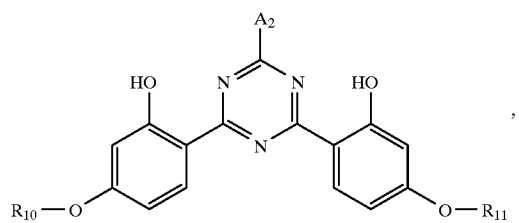
(4)

in which
$R_{10}$ and $R_{11}$, independently of one another, are hydrogen; $C_1$–$C_{18}$alkyl; $C_2$–$C_{18}$-alkenyl; a radical of the formula

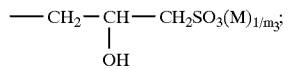

a radical of the formula —$CH_2$—$CH$(—$OH$)—$CH_2$—$O$—$T_1$; or a radical of the formula (4a)

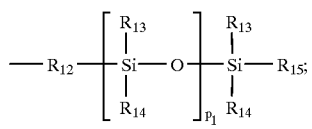

$R_{12}$ is a direct bond; straight-chain or branched $C_1$–$C_4$alkylene radical or a radical of the formula

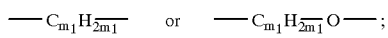

$R_{13}$, $R_{14}$ and $R_{15}$, independently of one another, are $C_1$–$C_{18}$alkyl; $C_1$–$C_{18}$alkoxy or a radical of the formula

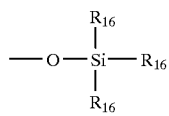

$R_{16}$ is $C_1$–$C_5$alkyl;
$m_1$ and $m_3$, independently of one another, are 1 to 4;
$p_1$ is 0 or a number from 1 to 5;
$T_1$ is hydrogen; or $C_1$–$C_8$alkyl;
$A_2$ is a radical of the formula

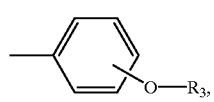
(4b)

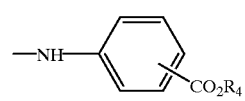
(4c)

or of the formula

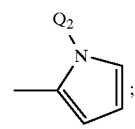
(4d)

in which
$R_3$ is hydrogen; $C_1$–$C_{10}$alkyl, —$(CH_2CHR_5$—$O)_n$—$R_4$, or a radical of the formula —$CH_2$—$CH$(—$OH$)—$CH_2$—$O$—$T_1$;
$R_4$ is hydrogen; M; $C_1$–$C_5$alkyl; or a radical of the formula —$(CH_2)_{m_2}$—$O$—$T_2$;
$R_5$ is hydrogen or methyl;
$T_1$ and $T_2$, independently of one another, are hydrogen or $C_1$–$C_8$alkyl;
$Q_2$ is $C_1$–$C_{18}$alkyl;
M is a metal cation;
$m_2$ is 1 or 2;
and
n is 1–16;
and cosmetically tolerable carriers or auxiliaries.

For cosmetic use, the sunscreens according to the invention usually have a mean particle size in the range from 0.02 to 2, preferably 0.05 to 1.5, and very particularly from 0.1 to 1.0μ. The insoluble UV absorbers according to the invention can be brought to the desired particle size by customary methods, e.g. grinding, using, for example, a jet, ball, vibration or hammer mill. Preferably, the grinding is carried out in the presence of 0.1 to 30, preferably 0.5 to 15% by weight, based on the UV absorber, of a grinding aid such as, for example, an alkylated vinylpyrrolidone polymer, a vinylpyrrolidone-vinyl acetate copolymer, an acyl glutamate or, in particular, a phospholipid.

Besides the UV absorbers according to the invention, the cosmetic compositions can additionally contain one or more further UV-protective substances, e.g. triazines, oxanilides, triazoles or amides containing vinyl groups or cinnamides. Such protective substances are described, for example, in GB-A-2,286,774 or alternatively are known from Cosmetics & Toiletries (107), 50 et seq. (1992).

The cosmetic compositions according to the invention contain 0.1 to 15, preferably 0.5 to 10% by weight, based on the total weight of the composition, of a UV absorber or of a mixture of UV absorbers and a cosmetically compatible auxiliary.

The cosmetic compositions can be prepared by physical mixing of the UV absorber(s) with the auxiliary by the usual methods, such as, for example, by simply stirring the individual components together.

The cosmetic compositions according to the invention can be formulated as a water-in-oil or oil-in-water emulsion, as an oil-in-alcohol lotion, as a vesicular dispersion of an ionic or non-ionic amphiphilic lipid, as a gel, solid stick or as an aerosol formulation.

As a water-in-oil or oil-in-water emulsion, the cosmetically compatible auxiliary preferably contains 5 to 50% of an oil phase, 5 to 20% of an emulsifier and 30 to 90% of water. The oil phase can in this case contain any oil suitable for cosmetic formulations, e.g. one or more hydrocarbon oils, a wax, a natural oil, a silicone oil, a fatty acid ester or a fatty alcohol. Preferred mono- or polyols are ethanol, isopropanol, propylene glycol, hexylene glycol, glycerol and sorbitol.

Any emulsifier which can be employed conventionally can be used for the cosmetic compositions according to the invention, e.g. one or more ethoxylated esters of natural derivatives, e.g. polyethoxylated esters of hydrogenated castor oil; or a silicone emulsifier such as silicone polyol; a free or ethoxylated fatty acid soap; an ethoxylated fatty alcohol; a free or ethoxylated sorbitan ester, an ethoxylated fatty acid; or an ethoxylated glyceride.

The cosmetic compositions can also contain further components such as emollients, emulsion stabilizers, skin moisturizers, skin bronzing accelerators, thickeners such as xanthan, moisture retention agents such as glycerol, preservatives, fragrances and colourants.

The cosmetic formulations according to the invention are distinguished by excellent protection of the human skin against the harmful influence of sunlight.

In the following examples, percentages are by weight. In the case of the bis(resorcinyl)triazine compounds employed, the amounts relate to the pure substance.

Examples of preparation of the novel compounds

EXAMPLE 1

2,4-Bis{[4-(2-ethylhexyloxy)-2-hydroxy]phenyl}-6-(4-methoxyphenyl)-1,3,5-triazine a) Grignard reaction: In a 500 ml sulfonating flask having a stirrer, dropping funnel, condenser and internal thermometer, 7.3 g (0.3 mol) of magnesium turnings and a few grains of iodine are initially introduced into 60 ml of dry tetrahydrofuran (THF). Under dry protective gas (nitrogen), 56.1 g (0.3 mol) of 4-bromoanisole, dissolved in 100 ml of THF, are slowly added dropwise at 60° C. After the complete dissolution of the Mg turnings, the mixture is stirred at 60° C. for 90 minutes. The Grignard solution is then added dropwise at 5° C. under nitrogen in the course of 60 minutes to a solution of 55.3 g (0.3 mol) of cyanuric chloride in 150 ml of THF. The mixture is evaporated to dryness at room temperature, 500 ml of dil. hydrochloric acid are allowed to run in and the mixture is extracted with 300 ml of methylene chloride. For working-up, the solvent is removed in vacuo, and the semisolid residue is tritrated with a little isopropanol and filtered off with suction. Purification is carried out by recrystallization from toluene/hexane (1:1). 62.8 g (82% of theory) of 6-(4-methoxyphenyl)-2,4-dichloro-1,3,5-triazine are obtained (m.p.: 131–134° C.).

b) Friedel-Crafts acylation: In a 750 ml sulfonation flask having a stirrer, dropping funnel, condenser and internal thermometer, 43.5 g (0.17 mol) of 6-(4-methoxyphenyl)-2,4-dichloro-1,3,5-triazine and 37.5 g (0.34 mol) of resorcinol are initially introduced into a mixture of 150 ml of xylene (isomer mixture) and 150 ml of sulfolane. At 60–65° C., 52.1 g (0.39 mol) of aluminium chloride are slowly introduced and the mixture is stirred until evolution of HCl is finished (about 4 hours). The warm reaction solution is allowed to run into 750 ml of methanol/350 ml of dil. hydrochloric acid with stirring, and the solid is filtered off with suction and washed with water until neutral. Drying takes place at 100° C. in vacuo. 61.1 g (89.1% of theory) of 2,4-bis(2,4-dihydroxyphenyl)-6-(4-methoxyphenyl)-1,3,5-triazine is obtained as a yellow powder.

c) Alkylation: In a 500 ml sulfonation flask having a stirrer, dropping funnel, condenser and internal thermometer, 20.2 g (0.05 mol) of 2,4-bis(2,4-dihydroxyphenyl)-6-(4-methoxyphenyl)-1,3,5-triazine are introduced together with 200 ml of methylcellosolve (Merck®) and 8.8 g (0.11 mol) of 50% sodium hydroxide solution. The mixture is stirred for 30 minutes at 80° C. and 23.2 g (0.12 mol) of 3-bromomethylheptane, dissolved in 25 ml of methylcellosolve, are slowly added dropwise at the same temperature. The alkylation can be monitored by thin-layer chromatography. After reaction for 8 hours at 112–114° C., the starting material can no longer be detected. The mixture is evaporated to dryness, the residue is taken up in 100 ml of toluene/hexane (7 vol./3 vol.) and the solution is filtered from insoluble material. For purification, it is chromatographed on silica gel (column: Ø=5 cm, I=60 cm). The compound of the formula (101) is obtained as a viscous, slightly yellow resin, which crystallizes after a few weeks.

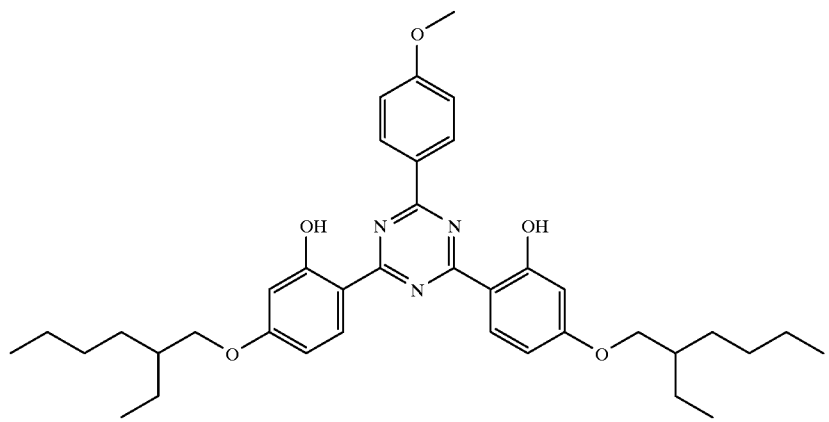

(101)

Yield: 24.6 g (78.4% of theory). Crystallization can be accelerated by addition of seed crystals.

Properties

Slightly yellow crystals, m.p.: 83–85 20 C.

UV spectrum: $\lambda_{max}$=343 nm, $\lambda_{max}$=47 000 $M^{-1}cm^{-1}$ (ethanol)

$^1$H-NMR spectrum: δ [ppm, $CDCl_3$]=0.8–1.0 (m, 12H, —$CH_3$), 1.2–1.8 (m, 18H, —$CH_2$— and —CH—), 3.8–3.9 (d, s, 7H, —O—$CH_2$— and —O—$CH_3$), 6.4–8.6 (10H, aromatics), 13.2–13.6 (s, 2H, —OH)

EXAMPLE 2

The procedure is as described in Example 1c), with the difference that for the alkylation 17.8 g of 3-chloromethylheptane, dissolved in 25 ml of DMF, are used instead of 3-bromomethylheptane.

EXAMPLE 3

2,4-Bis{[4-(3-sulfonato-2-hydroxypropyloxy)-2-hydroxy]phenyl}-6-(4-methoxyphenyl)-1,3,5-triazine sodium salt In a 500 ml sulfonation flask having a stirrer, dropping funnel, condenser and internal thermometer, 8.1 g (0.02 mol) of 2,4-bis(2,4-dihydroxyphenyl)-6-(4-methoxyphenyl)-1,3,5-triazine are initially introduced together with 100 ml of methylcellosolve (Merck®) and 3.36 g (0.04 mol) of 50% sodium hydroxide solution. The mixture is stirred at 80° C. for 30 minutes and 9.44 g (0.048 mol) of Hoffmann acid are added in small portions at the same temperature. The alkylation can be monitored by thin-layer chromatography. After reaction at 102–103° C. for 18 hours, the starting material can no longer be detected. The mixture is rendered weakly alkaline with a few drops of 2N sodium hydroxide solution and the reaction solution is allowed to run into 50 ml of acetone at 60° C. The precipitate is filtered off with suction and washed several times with acetone. Drying is carried out at 100° C. in vacuo. Yield: 10.8 g (74.6% of theory) of yellow, strongly hygroscopic powder.

Properties

UV spectrum: $\lambda_{max}$=324–333 nm, $\lambda_{max}$=40 000 $M^{-1}$ $cm^{-1}$ (water)

The structure is in agreement with the elemental analysis and $^1$H-NMR spectrum.

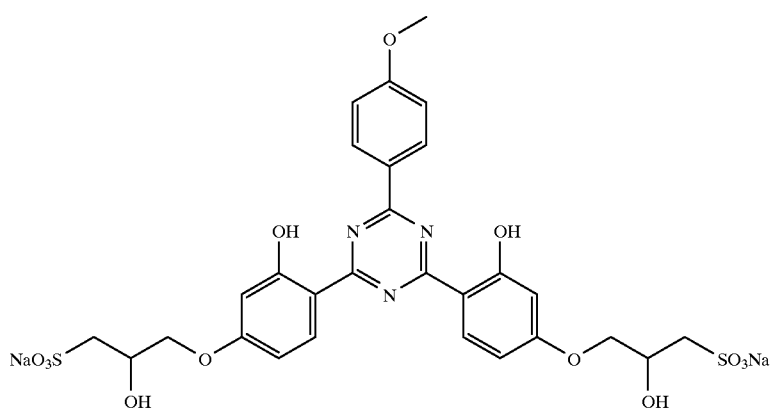

(102)

Preparation is carried out by alkylation of 2,4-bis(2,4-dihydroxyphenyl)-6-(4-methoxyphenyl)-1,3,5-triazine (cf. Example 1b) with 1-chloro-2-propanol-3-sulfonic acid sodium salt ("Hoffmann acid").

EXAMPLE 4

2,4-Bis{[4-(3-(2-propyloxy)-2-hydroxypropyloxy)-2-hydroxy]phenyl}-6-(4-methoxyphenyl)-1,3,5-triazine

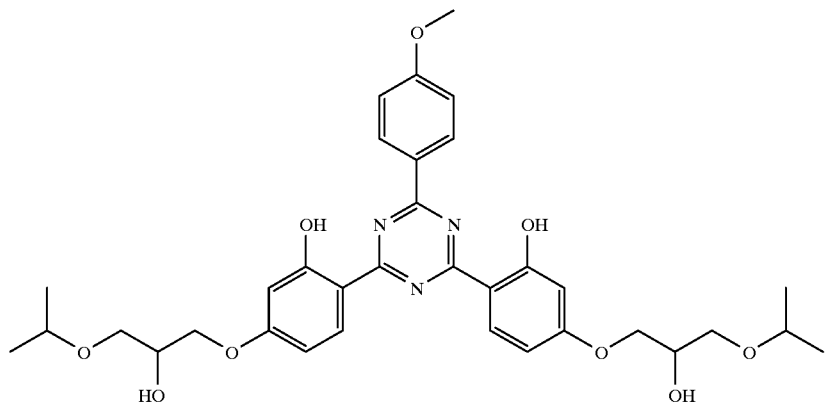

(103)

Preparation is carried out by acid-catalysed addition of isopropyl glycidyl ether to 2,4-bis(2,4-dihydroxyphenyl)-6-(4-methoxyphenyl)-1,3,5-triazine (cf. Example 1b).

In a 250 ml sulfonation flask having a stirrer, dropping funnel, condenser and internal thermometer, 8.1 g (0.02 mol) of 2,4-bis(2,4-dihydroxyphenyl)-6-(4-methoxyphenyl)-1,3,5-triazine are initially introduced together with 5.1 g (0.044 mol) of 2,3-epoxypropyl isopropyl ether and 0.7 g of ethyltriphenylphosphonium bromide in 80 ml of xylene/20 ml of dimethylformamide. The mixture is heated to reflux temperature (130–132° C.). After a reaction time of 14 hours, the reaction has ended (thin-layer chromatogram). The mixture is evaporated to dryness, the residue is dissolved in 50 ml of toluene/acetone (75 vol./25 vol.) and the mixture is chromatographed on silica gel (column: Ø=4 cm, I=40 cm). The compound of the formula (103) is obtained as a viscous, slightly yellowish resin, which crystallizes after a few weeks. Yield: 7.9 g (62.2% of theory). Crystallization can be accelerated by addition of seed crystals.

Properties

Slightly yellow crystals, m.p.: 95–98° C.

UV spectrum: $\lambda_{max}$=341 nm, $\lambda_{max}$=50 000 $M^{-1}cm^{-1}$ (ethanol)

$^1$H-NMR spectrum: δ [ppm, $CDCl_3$]=1.2–1.3 (d, 12H, —$CH_3$), 3.6–3.8 (m, 6H, —$CH_2$—O— and —O—CH—), 3.9 (s, 3H, —O—$CH_3$), 4.1–4.3(m, 6H, Ph—O—$CH_2$—CH—), 6.4–8.6 (10H, aromatics), 13.2–13.6 (s, 2H, Ph—OH)

EXAMPLE 5

2,4-Bis{[4-(2-ethylhexyloxy)-2-hydroxy]phenyl}-6-[4-(2-methoxyethylcarboxyl)phenylamino]-1,3,5-triazine a) 2,4-Dichloro-6-[4-(ethylcarboxyl)phenylamino]-1,3,5-triazine: In a 2 l flat-flange reactor having a stirrer, internal thermometer, dropping funnel, pH electrode and metering pipette (metering apparatus coupled to pH measuring apparatus), 92.2 g (0.5 mol) of cyanuric chloride are completely dissolved in 750 ml of acetone and the solution is cooled to 0–5° C. 75 ml of dist. water are added and 82.6 g (0.5 mol) of ethyl 4-aminobenzoate, dissolved in 150 ml of acetone, are added dropwise to the thick suspension in the course of 45 minutes. During the addition, the pH is kept constant at pH=4.0–4.5 by automatic metering in of 30% NaOH; the reaction temperature is kept between 0–5° C. by cooling (ice/sodium chloride). The mixture is then stirred without cooling for 3 hours, the temperature climbing to room temperature. The solid is filtered off with suction, washed with several portions of water and acetone and dried at 80° C. in vacuo. Yield: 132.5 g (84.6% of theory).

Properties

Beige powder of m.p.: 286–287° C. (decomposition).

The elemental analysis values (C, H, N, Cl) are in agreement with the empirical formula $C_{12}H_{10}Cl_2N_4O_2$.

b) Friedel-Crafts acylation: In a 1.5 l sulfonation flask having a stirrer, dropping funnel, condenser and internal thermometer, 125.3 g (0.4 mol) of 2,4-dichloro-6-[4-(ethylcarboxyl)-phenylamino]-1,3,5-triazine are suspended in 500 ml of nitrobenzene at room temperature. 117.3 g (0.88 mol) of aluminium chloride (for synthesis, Merck) are added in the course of 1 minute, the temperature climbing to 48° C. A solution of 105.7 g (0.96 mol) of resorcinol in 160 ml of sulfolane is added dropwise at this temperature in the course of 2 hours and the mixture is stirred for a further 4 hours. The clear, red-brown solution (72° C.) is cooled to 50° C. and, for hydrolysis of the Friedel-Crafts complex, stirred into a mixture of 1500 ml of methanol, 150 ml of conc. HCl and 150 ml of water. The mixture is allowed to stand overnight and the solid is filtered off with suction. For purification, the precipitate is stirred twice in 1500 ml of acetone/300 ml of water at 50° C., washed with acetone/water until neutral and dried at 100° C. in vacuo. Yield: 136.5 g of 2,4-bis(2,4-dihydroxyphenyl)-6-[4-(ethylcarboxyl)phenylamino]-1,3,5-triazine (74.1% of theory).

Properties

Yellow powder of m.p.>300° C.

The elemental analysis values (C, H, N, O) are in agreement with the empirical formula $C_{24}H_{20}Cl_{12}N_4O_6$.

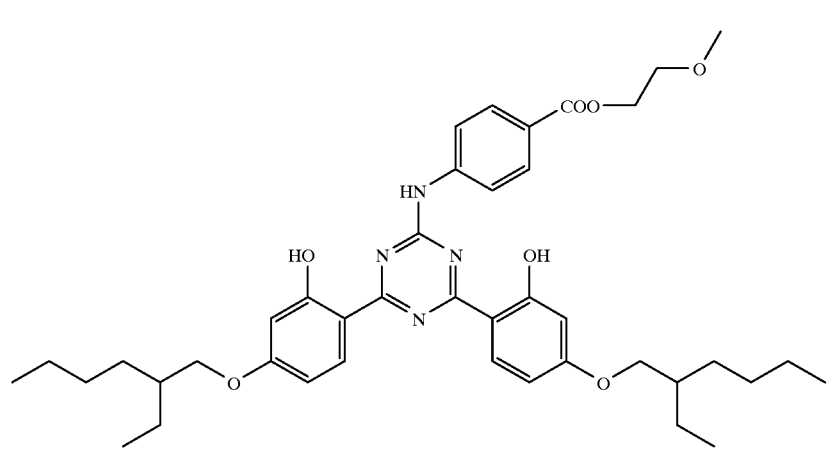

(104)

c) Alkylation/transesterification: In a 250 ml sulfonation flask having a stirrer, dropping funnel, condenser and internal thermometer, 11.5 g (0.025 mol) of 2,4-bis(2,4-dihydroxyphenyl)-6-[4-(ethylcarboxyl)phenylamino]-1,3,5-triazine are initially introduced together with 100 ml of methylcellosolve (Merck®) and 7.0 g (0.05 mol) of 30% sodium hydroxide solution. The mixture is stirred at 80° C. for 30 minutes and 12.6 g (0.065 mol) of 3-bromomethylheptane, dissolved in 10 ml of methylcellosolve, are slowly added dropwise at the same temperature. The alkylation/transesterification can be monitored by thin-layer chromatography. After reaction at 102–103° C. for 5 hours, the starting material can no longer be detected. The mixture is evaporated to dryness, the residue is taken up in 20 ml of toluene/ethyl acetate (3 vol./1 vol.) and filtered from undissolved material. For purification, it is chromatographed on silica gel (column: Ø=5 cm, I=60 cm). The compound of the formula (104) is obtained as a slightly yellow, crystalline substance. Yield: 1.8 g (10.5% of theory).

Properties

Melting point: 165–166° C.

UV spectrum: $\lambda_{max}$=334 nm, $\lambda_{max}$=52 000 $M_{-1}cm^{-1}$ (ethanol)

The structure is in agreement with elemental analysis and $^1$H-NMR spectrum.

EXAMPLE 6

2,4-Bis{[4-(3-(2-propyloxy)-2-hydroxypropyloxy)-2-hydroxy]phenyl}-6-[4-ethylcarboxyl)phenylamino]-1,3,5-triazine mol) of 2,4-bis(2,4-dihydroxyphenyl)-6-[4-(ethylcarboxyl)phenylamino]-1,3,5-triazine are initially introduced into 140 ml of xylene together with 7.7 g (0.066 mol) of 2,3-epoxypropyl isopropyl ether and 1.0 g of ethyltriphenylphosphonium bromide. The mixture is heated to reflux temperature (130–132° C.). After a stirring time of 20 hours, the reaction has ended (thin-layer chromatogram). The mixture is evaporated to dryness, the residue is dissolved in 80 ml of methylene chloride/methanol (95 vol./5 vol.) and the mixture is chromatographed on silica gel (column: Ø=5 cm, I=45 cm). The compound of the formula (105) is obtained as a viscous, slightly yellowish resin, which crystallizes after stirring with hexane. Yield: 7.3 g (35.1% of theory).

Properties

Slightly yellow crystals, melting point: 175–177° C.

(105)

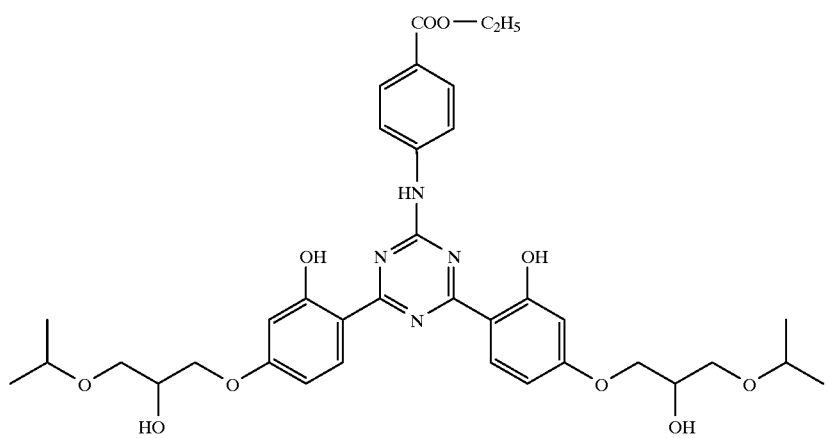

Preparation is carried out by acid-catalysed addition of isopropyl glycidyl ether to 2,4-bis(2,4-dihydroxyphenyl)-6-[4-(ethylcarboxyl)phenylamino]-1,3,5-triazine (cf. Example 4b)).

In a 250 ml sulfonation flask having a stirrer, dropping funnel, condenser and internal thermometer, 13.8 g (0.03

UV spectrum: $\lambda_{max}$=334 nm, $\lambda_{max}$=47 000 $M_{-1}cm^{-1}$ (ethanol) H-NMR spectrum: agrees with the proposed structure

EXAMPLE 7

2,4-Bis{[4-(2-ethylhexyloxy)-2-hydroxy]phenyl}-6-(1-methylpyrrol-2-yl)-1,3,5-triazine (106)

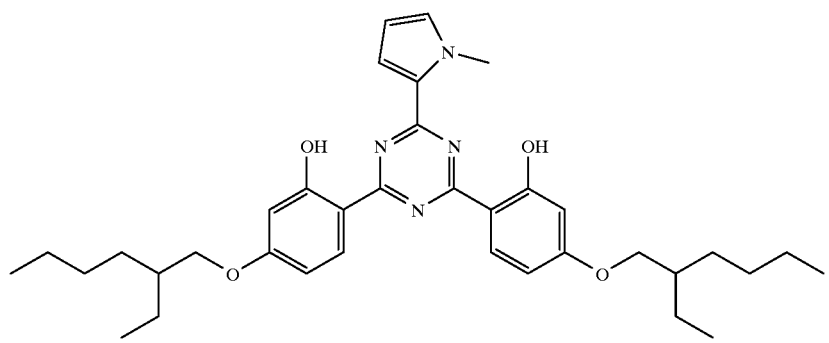

a) 2,4-Dichloro-6-(1-methylpyrrol-2-yl)-1,3,5-triazine: In a 500 ml sulfonation flask having a stirrer, dropping funnel, condenser and internal thermometer, 46.1 g (0.25 mol) of cyanuric chloride are initially introduced into 200 ml of toluene and slowly treated with 21.1 g (0.26 mol) of 1-methylpyrrole. The mixture is heated to reflux temperature (110–114° C.) and stirred for 6 hours until the evolution of HCl has ended. After cooling, it is extracted first with dil. sodium carbonate solution, then extracted by shaking with water. The organic phase is dried over sodium sulfate and evaporated to dryness, and the residue is stirred in 750 ml of n-hexane. The crystals are filtered off with suction and dried at 60° C. in vacuo. Yield: 23.0 g (40.2% of theory).

Properties

Slightly brown crystals: m.p.: 155–156° C.

b) Friedel-Crafts acylation: In a 500 ml sulfonation flask having a stirrer, dropping funnel, condenser and internal thermometer, 22.9 g (0.1 mol) of 2,4-dichloro-6-(1-methylpyrrol-2-yl)-1,3,5-triazine and 24.2 g (0.22 mol) of resorcinol are initially introduced into 200 ml of xylene (isomer mixture). At 45–50° C., 29.3 g (0.22 mol) of aluminium chloride are slowly introduced and the mixture is stirred at 80–83° C. until the evolution of HCl has ended (about 2 hours). The warm reaction solution is allowed to run into dil. hydrochloric acid with stirring, and the solid is filtered off with suction and washed with acetone/water until neutral. Drying is carried out at 100° C. in vacuo. 30.5 g (81.0% of theory) of 2,4-bis(2,4-dihydroxyphenyl)-6-(1-methylpyrrol-2-yl)-1,3,5-triazine are obtained as a yellow powder (m.p.>300° C.). The structure is in agreement with the $^1$H-NMR spectrum.

c) Alkylation: In a 250 ml sulfonation flask having a stirrer, dropping funnel, condenser and internal thermometer, 7.53 g (0.02 mol) of 2,4-bis(2,4-dihydroxyphenyl)-6-(1-methylpyrrol-2-yl)-1,3,5-triazine are initially introduced at room temperature together with 80 ml of methylcellosolve (Merck®) and 5.6 g (0.04 mol) of 30% sodium hydroxide solution. The mixture is stirred at 80° C. for 30 minutes and 9.5 g (0.048 mol) of 3-bromomethylheptane, dissolved in 25 ml of methylcellosolve, are slowly added dropwise at the same temperature. The alkylation can be monitored by thin-layer chromatography. After reaction at 110–112° C. for 6 hours, the starting material can no longer be detected. The mixture is evaporated to dryness, the residue is taken up in 100 ml of toluene/acetone (7 vol./3 vol.) and filtered from insoluble material. For purification, it is chromatographed on silica gel (column: Ø=5 cm, l=60 cm). The compound of the formula (106) is obtained as a viscous, slightly yellow resin, which crystallizes after some time. Yield: 5.8 g (48.3% of theory). Crystallization can be accelerated by addition of seed crystals.

Properties

Slightly yellow crystals; m.p.: 95–96° C.

UV spectrum: $\lambda_{max}$=349 nm, $\lambda_{max}$=71 000 $M^{-1}cm^{-1}$ (ethanol)

$^1$H-NMR spectrum: δ [ppm, $CDCl_3$]=0.8–1.0 (m, 12H, —$CH_3$), 1.2–1.8 (m, 18H, —$CH_2$— and —CH—), 3.8–3.9 (d, 4H, —O—$CH_2$—), 4.15 (s, 3H, N—$CH_3$), 6.4–8.6 (9H, aromatics), 13.5 (s, 2H, —OH)

EXAMPLE 8

2,4-Bis{[4-(tris(trimethylsiloxysilylpropyloxy)-2-hydroxy]phenyl}-6-(4-methoxyphenyl)-1,3,5-triazine

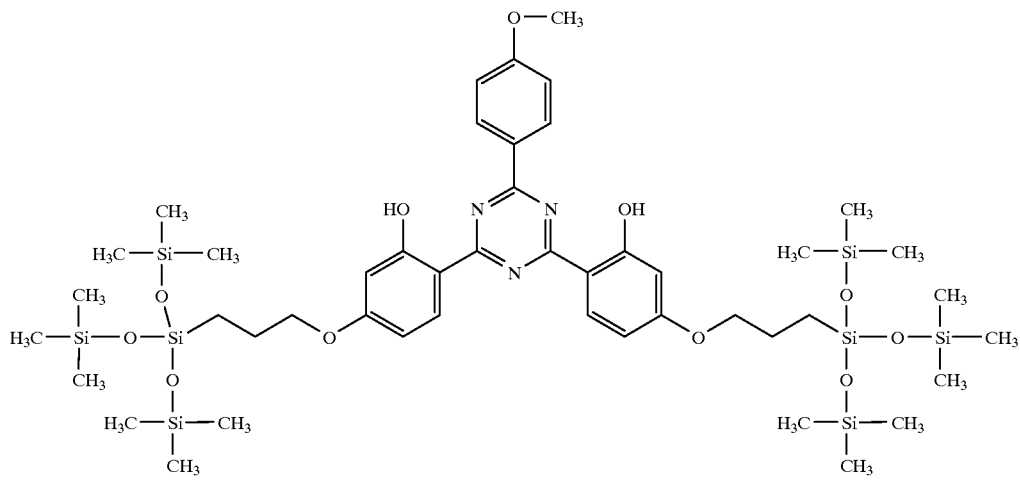

(107)

In a 50 ml sulfonation flask having a stirrer, dropping funnel, condenser and internal thermometer, 100 mg (0.248 mmol) of 2,4-bis(2,4-dihydroxyphenyl)-6-(4-methoxyphenyl)-1,3,5-triazine are initially introduced with 5 ml of dimethylformamide and 69.2 mg (0.496 mmol) of calcium carbonate. The yellow suspension is heated to 80° C. and stirred for 1 hour. At the same temperature, 1.91 g (4.96 mmol) of 3-chloropropyl-tris(trimethylsiloxy)silane are slowly added dropwise. The mixture is stirred at 80° C. for several hours and the conversion is monitored by thin-layer chromatography (TLC mobile phase: toluene/ethyl acetate 7:3). After 5 hours, any further conversion is no longer to be found. For working-up, the solution is concentrated and purified by column chromatography (50 g of silica gel, eluent toluene/ethyl acetate 10:1 v/v).

Yield: 14 mg (5.2%), colourless oil.

$^1$H NMR ($CDCl_3$): δ (ppm): 0–2.5 (in each case m, 62H, Si—$CH_3$, Si—($CH_2$)$_2$), 3.5–3.8 (2×m, in each case 2H, O$CH_2$—), 3.9 (s, 3H, —O$CH_3$), 6.4–8.2 (m, 10H, aromatics, 13.4–13.5 (s, broad, 2H, OH)

$C_{46}H_{81}N_3O_{11}Si_8$ (1076.86)

EXAMPLE 9

2,4-Bis{[4-(2"-methylpropenyloxy)-2-hydroxy]phenyl}6-(4-methoxyphenyl)-1,3,5-triazine (108)

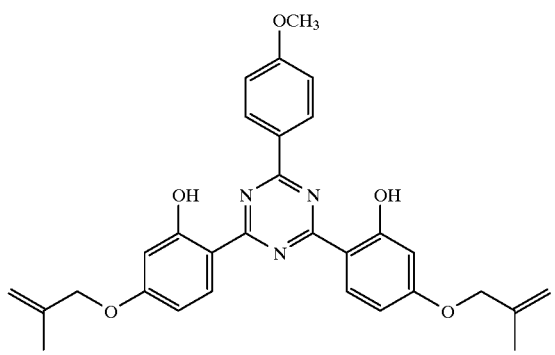

In a 1 l sulfonation flask having a stirrer, dropping funnel, condenser and internal thermometer, 23 g (0.057 mol) of 2,4-bis(2,4-dihydroxyphenyl)-6-(4-methoxyphenyl)-1,3,5-triazine are dissolved in 450 ml of dimethylformamide. Into this yellow solution are introduced 15.92 g (0.1–mol) of potassium carbonate which have been finely ground in a mortar. The solution is heated in the course of 1 hour to an internal temperature of 100° C. 10.33 g (0.114 mol) of methallyl chloride are added dropwise in the course of 15 minutes to the reddish solution obtained. The reaction mixture is stirred at 100° C. for about 2.5 hours and at room temperature for 8 hours. The conversion is monitored by thin-layer chromatography (TLC mobile phase toluene/ethyl acetate 10:1). The starting material disappears completely.

For working up, the reaction solution is filtered through a paper filter and the residue is washed with a little toluene. The filtrate is treated with the same amount of toluene and concentrated. 37 g of crude product are obtained, which is separated by column chromatography (2 kg of silica gel, eluent: about 9 l of toluene/ethyl acetate 25:1, then 8 l of toluene/ethyl acetate 10:1, v/v). Besides the desired disubstituted methallyl derivative, the mono- and trisubstituted derivatives can also be isolated as secondary components.

Yield: 4.77 g (16%), yellowish amorphous solid.

$^1$H NMR (CDCl$_3$): δ(ppm): 1.9 (s, 6H, —C$\underline{H}_3$), 3.5–3.8 (2×m, in each case 2H, OC$\underline{H}_2$—), 3.9 (s, 3H, —OC$\underline{H}_3$), 4.3–4.4 (s, 4H, —OC$\underline{H}_2$), 5.0–5.2 (2×s, C$\underline{H}_2$=), 6.4–8.2 (m, 10H, aromatics, 13.4–13.5 (s, broad, 2H, O$\underline{H}$)

C$_{30}$H$_{29}$N$_3$O$_5$ (511.56), correct elemental analysis

EXAMPLE 10

2,4-Bis{[4-(1',1',1',3',5',5',5'-heptamethyltrisiloxy-2"-methylpropyloxy)-2-hydroxy]-phenyl}-6-(4-methoxyphenyl)-1,3,5-triazine (109)

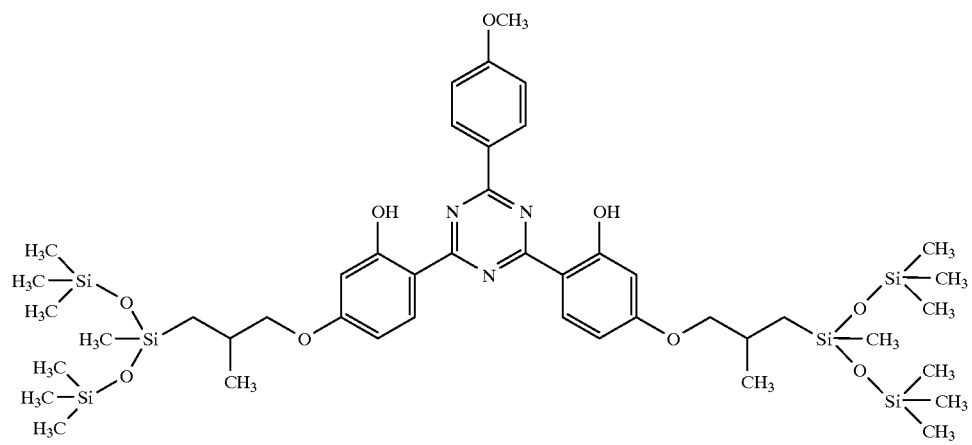

Preparation is carried out with exclusion of oxygen and moisture in an argon atmosphere. In a 1 l multinecked flask which has been heated thoroughly and cooled in a stream of argon, 12 g (23.46 mmol) of 2,4-bis{[4-(2"-methylpropenyloxy)-2-hydroxy]phenyl}-6-(4-methoxyphenyl)-1,3,5-triazine (obtained from Example 9) are completely dissolved in 600 ml of absolute toluene (dried over molecular sieve 4 Å). To this solution are cautiously added about 4.5 ml of catalyst solution (platinum-divinyltetramethyldisiloxane complex, ABCR PC 072, content 20 mg/10 ml, corresponds to 500 ppm of catalyst/mol equivalent of starting material), then 10.42 g (46.92 mmol) 1,1,1,3,5,5,5-heptamethyltrisiloxane (Fluka) are slowly added dropwise in the course of 5 hours. The clear yellow solution is heated at 80° C. for 2 hours. After a reaction period of 2 hours, the starting material has disappeared and a new main product has been formed (TLC mobile phase: n-hexane/ethyl acetate 15:1). The reaction solution is concentrated. 23.5 g of crude product are obtained, which is purified by column chromatography (900 g of silica gel, eluent n-hexane/ethyl acetate 15:1 v/v). The combined fractions are concentrated, dried, taken up in 300 ml of dioxane, filtered through Hyflo and freeze-dried. The lyophilizate is dried at 40–50° C. for 2 days in a high vacuum.

Yield: 10.3 g (46%), yellowish highly viscous oil.

UV spectrum: $\lambda_{max}$=356 nm, $\lambda_{max}$=47120 (n-hexane)

$^1$H NMR spectrum (CDCl$_3$): $\delta$(ppm): 0–0.2 (m, 42H, Si—C$\underline{H}_3$), 0.3, 0.6 (m, in each case 2H, Si—C$\underline{H}_2$), 1.0 (d, 6H, C$\underline{H}_3$—CH), 2.0 (m, 2H, C$\underline{H}$—CH$_3$), 3.5–3.8 (2×m, in each case 2H, OC$\underline{H}_2$—), 3.8 (s, 3H, OC$\underline{H}_3$), 6.4–8.2 (m, 10H, aromatics, 13.4–13.5 (s, broad, 2H, O$\underline{H}$)

$C_{44}H_{73}N_3O_9Si_6$ (956.58)

M$^+$ (EI): 957 (M+H)$^+$

Elemental analysis:

|  | C | H | N |
|---|---|---|---|
| calculated | 55.25% | 7.69% | 17.6% |
| found | 55.18% | 7.78% | 17.2% |

Application Examples

Use examples for cosmetic sun protection

The sun protection factors were determined according to the method of Diffey and Robson J. Soc. Cosmet. Chem. 40, 127–133 (1989) using an SPF analyser (Optometrix, SPF 290)

To determine the photostabilities, the filter substances are dissolved in ethanol (c=1·10$^{-5}$–5·10$^{-5}$M) and irradiated ($I_{UVB}$=0.4–8.0 mW/cm$^2$) with stirring using a metal halide lamp (Macam). To convert to the solar spectrum (CIE D65-normal daylight, standardized to $I_{UVB}$=0, 127 mW/cm$^2$), the integral over the products of the wavelength-resolved lamp intensity and the corresponding absorption values of the respective UV absorber between 290 and 400 nm is calculated and divided by the integral over the products of the D65 light intensities and the corresponding absorption values of the particular UV absorber in the range between 290 and 400 nm. The half-life for decomposition under irradiation with the metal halide lamp is multiplied by this factor in order to obtain the corresponding half-life under solar irradiation. The half-life for photodecomposition under lamp irradiation is determined by UV-spectroscopic measurement of the extinction at the wavelength of the maximum absorption and subsequent exponential fit. Using the process described, the half-lives for photodecomposition in the D65 light are thus obtained.

EXAMPLE 11 o/w emulsion with the compounds of the formulae (101), (103) and (106)

| (A): | |
|---|---|
| Triazine UV absorber | 3 g |
| Sesame oil | 10 g |
| Glyceryl stearate | 4 g |
| Stearic acid | 1 g |
| Cetyl alcohol | 0.5 g |
| Polysorbate 20 | 0.2 g |

-continued

| (B): | |
|---|---|
| Propylene glyool | 4 g |
| Propylparaben | 0.05 g |
| Methylparaben | 0.15 |
| Triethanolamine | 0.1 g |
| Carbomer 934 | 0.1 g |
| Water | to 100 ml |

Preparation of the emulsion

Phase (A)

The UV absorber is first dissolved in sesame oil. The other components of (A) are added and fused together.

Phase (B)

Propylparaben and methylparaben are dissolved in propylene glycol. 60 ml of water are then added, the mixture is heated to 70° C. and carbomer 934 is emulsified therein.

Emulsion (A) is slowly added to B with vigorous mechanical energy input. The volume is adjusted to 100 ml by addition of water.

The determined sunscreen factors and photostabilities can be taken from Table 1.

TABLE 1

|  | Concentration | Sunscreen factor* | Photostability** [h] |
|---|---|---|---|
| Compound of the formula (101) | 3% | 9.1 | 1500 |
| Compound of the formula (103) | 3% | 9.6 | 1500 |
| Compound of the formula (106) | 3% | 6.2 | 360 |

*according to Diffey and Robson
**as the half-life of photodecomposition in the D65 light in ethanolic solution The sunscreen factor can be varied using the UV absorber concentration.

The results show that the active substances have a high photostability and a good sunscreen factor can be achieved even at low concentration.

EXAMPLE 12 w/o emulsion with the compound of the formula (102)

| (A): | |
|---|---|
| Methylglucose isostearate | 3 g |
| Mineral oil | 15 g |
| Octyl octanoate | 5 g |
| PEG-45/dodecyl glycol copolymer | 1 g |
| (B): | |
| Triazine UV absorber | 3 g |
| Glycerol | 3 g |
| Propylene glycol | 3 g |
| Magnesium sulfate | 0.7 g |
| Deionized water | 61.35 g |
| (C): | |
| Perfume | 0.3 g |
| Methyldibromoglutaronitrile and phenoxyethanol | 0.15 g |

The phases (A) and (B) are first prepared separately at 80° C. (B) is then added to (A) with continuous energy input and subsequently homogenized for 3 min. Finally (C) is added at 35° C.

The determined sunscreen factors and photostabilities can be taken from Table 2.

TABLE 2

| | Concentration | Sunscreen factor* | Photostability** [h] |
|---|---|---|---|
| Compound of the formula (102) | 3% | 5.6 | 6100 |

*according to Diffey and Robson
**as the half-life of photodecomposition in the D65 light in ethanolic solution The sunscreen factor can be varied using the UV absorber concentration.

The results show that the active substances have a high photostability and a good sunscreen factor can be achieved even at low concentration.

EXAMPLE 13
suspensions of compounds of the formulae (104) and (105)

| Triazine UV absorber | 3 g |
|---|---|
| $C_9$–$C_{19}$-fatty alcohol polyglucosides | 2.4 g |
| Sodium chloride | 1 g |
| Xanthan gum | 0.5 g |
| Bronopol | 0.1 g |
| Deionized water | 93 g | preparation of the formulation 40 g of the UV absorber, 20 g of the fatty alcohol polyglucoside and 40 g of water are mixed and ground using a ball mill (Drais) such that the particle size is less than 1 μm. Starting from this paste, the other components are correspondingly admixed according to the above recipe.

The determined sunscreen factors and photostabilities can be taken from Table 3.

TABLE 3

| | Concentration | Sunscreen factor* | Photostability** [h] |
|---|---|---|---|
| Compound of the formula (104) | 3% | 9.4 | 250 |
| Compound of the formula (105) | 3% | 5.1 | 270 |

*according to Diffey and Robson
**as the half-life time of photodecomposition in the D65 light in ethanolic solution The sunscreen factor can be varied using the UV absorber concentration.

The results show that the active substances have a high photostability and a good sunscreen factor can be achieved even at low concentration.

What is claimed is:

1. A bis(resorcinyl)triazine of the formula

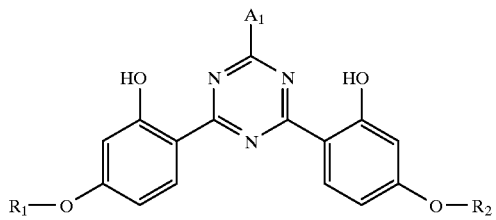
(1)

in which $R_1$ and $R_2$, independently of one another, are $C_3$–$C_{18}$alkyl; a radical of the formula —$CH_2$—$CH$(—OH)—$CH_2$—O—$T_1$; or $R_1$ and $R_2$ are a radical of the formula

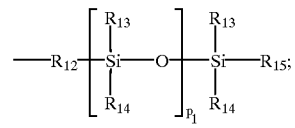
(4a)

$R_{12}$ is a direct bond; a straight-chain or branched $C_1$–$C_4$alkylene radical or a radical of the formula

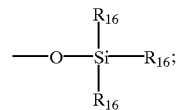

$R_{13}$, $R_{14}$ and $R_{15}$, independently of one another, are $C_1$–$C_{18}$alkyl; $C_1$–$C_{18}$alkoxy or a radical of the formula

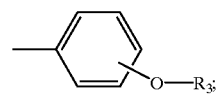

$R_{16}$ is $C_1$–$C_5$alkyl;

$m_1$ is 1 to 4;

$p_1$ is 0 or a number from 1 to 5;

$A_1$ is a radical of the formula

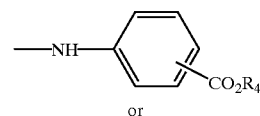
(1b)

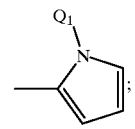
(1c)

or (1d)

$R_3$ is hydrogen; or $C_1$–$C_{10}$alkyl;

$R_4$ is hydrogen; M; $C_1$–$C_5$alkyl; or a radical of the formula —$(CH_2)_{m_2}$—O—$T_1$;

$R_5$ is hydrogen; or methyl;

$T_1$ is hydrogen; or $C_1$–$C_8$alkyl;

$Q_1$ $C_1$–$C_{18}$alkyl;

M is a metal cation;

$m_2$ is 1 to 4; and $n_1$ is 1–16;

with the proviso that the compound of formula (1) is excluded wherein $R_3$ is $CH_3$ and $R_1$ and $R_2$ are both $CH_2CH(OH)CH_2OC_4H_9$.

2. A bis(resorcinyl)triazine according to claim 1, wherein $A_1$ is a radical of the formula

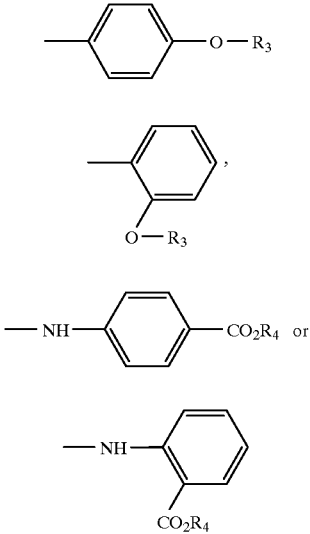

in which $R_3$ and $R_4$ are as defined in claim 1.

3. A bis(resorcinyl)triazine according to claim 1 of the formula

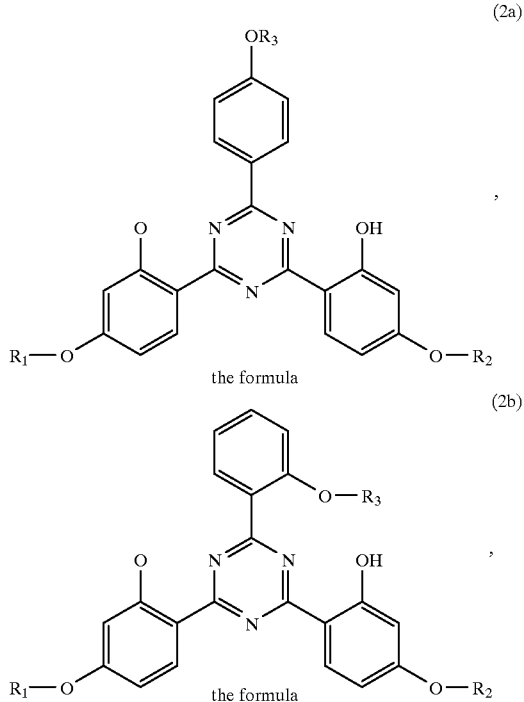

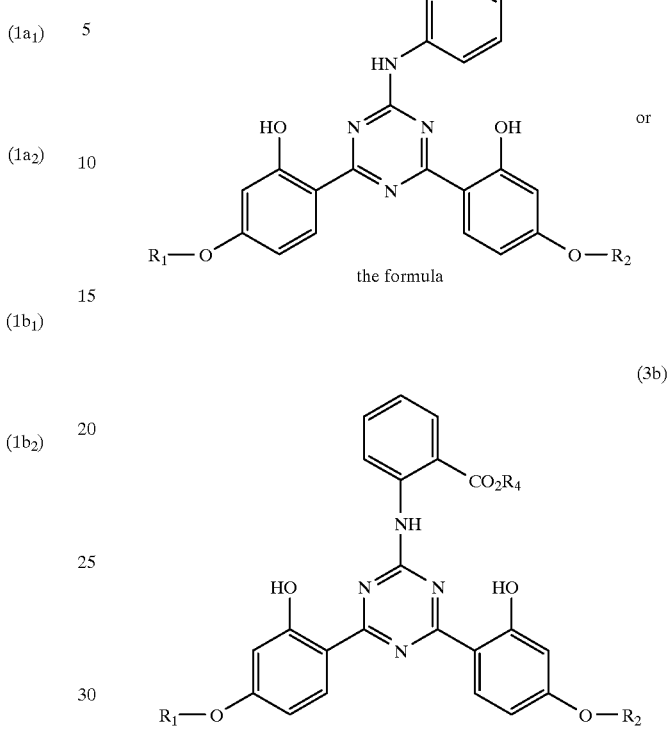

in which $R_1$ and $R_2$, independently of one another, are $C_3$–$C_{18}$alkyl; or —$CH_2$—CH(—OH)—$CH_2$—O—$T_1$;

$R_3$ is $C_1$–$C_{10}$alkyl;

$R_4$ is hydrogen; M; $C_1$–$C_5$alkyl; or a radical of the formula —$(CH_2)_m$—O—$T_1$;

M is a metal cation;

$T_1$ is hydrogen; or $C_1$–$C_5$alkyl; and m is 1 to 4.

4. A bis(resorcinyl)triazine according to claim 3, wherein in the formulae (2a) and (2b), $R_2$ and $R_1$, independently of one another, are $C_3$–$C_{18}$alkyl or —$CH_2$—CH(—OH)—$CH_2$—O—$T_1$;

$R_3$ is $C_1$–$C_{10}$alkyl; and $T_1$ is hydrogen; or $C_1$–$C_5$alkyl.

5. A bis(resorcinyl)triazine according to claim 3, wherein in the formula (3a) or (3b), $R_1$ and $R_2$ have the same meaning.

6. A method for protecting human and animal hair and skin from the harmful effects of UV radiation by treating the hair and the skin with bis(resorcinyl)triazines of the formula (4)

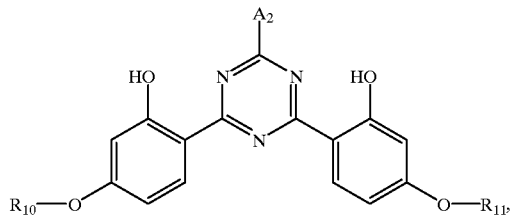

in which $R_{10}$ and $R_{11}$, independently of one another, are hydrogen; $C_1$–$C_{18}$alkyl; a radical of the formula

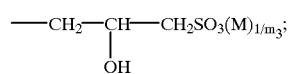

a radical of the formula —$CH_2$—$CH(—OH)$—$CH_2$—O—$T_1$; or a radical of formula (4a)

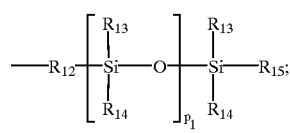

$R_{12}$ is a direct bond; straight-chain or branched $C_1$–$C_4$alkylene radical or a radical of the formula

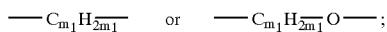

$R_{13}$, $R_{14}$ and $R_{15}$, independently of one another, are $C_1$–$C_{18}$alkyl; $C_1$–$C_{18}$alkoxy or a radical of formula

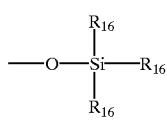

$R_{16}$ is $C_1$–$C_5$alkyl;
$m_1$ and $m_3$, independently of one another, are 1 to 4;
$p_1$ is 0 or a number from 1 to 5; and
$A_2$ is a radical of the formula (4b)

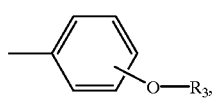

-continued (4c)

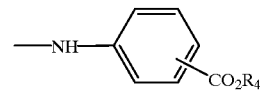

or the formula (4d)

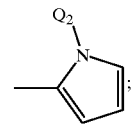

in which $R_3$ is hydrogen or $C_1$–$C_{10}$alkyl;
$R_4$ is hydrogen; M; $C_1$–$C_5$alkyl; or a radical of the formula —$(CH_2)_{m_2}$—O—$T_2$;
$R_5$ is hydrogen or methyl;
$T_1$ and $T_2$, independently of one another, are hydrogen or $C_1$–$C_8$alkyl;
$Q_2$ is $C_1$–$C_{18}$alkyl;
M is a metal cation and
$m_2$ is 1 or 2.

7. A cosmetic preparation, comprising at least one or more compounds of the formula (4) according to claim 6 with cosmetically tolerable carriers or auxiliaries.

8. A preparation according to claim 7, which contains UV-protective substances.

9. A preparation according to claim 8, which, as further UV-protective substances, contains triazines which are not of the formula (4), oxanilides, triazoles, amides containing vinyl groups or cinnamides.

10. A bis(resorcinyl)triazine of the formula:

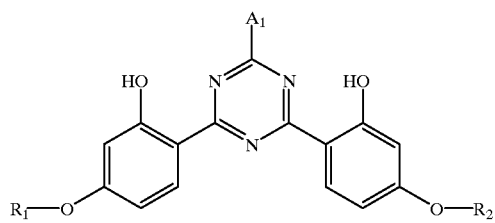

in which $R_1$ and $R_2$ are both $CH_2CH(C_2H_5)CH_2CH_2CH_2CH_3$, and $A_1$ is

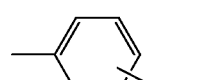

* * * * *